(12) United States Patent
Esnouf et al.

(10) Patent No.: US 10,549,054 B2
(45) Date of Patent: Feb. 4, 2020

(54) ARTIFICIAL AIRWAY

(75) Inventors: Philip Stuart Esnouf, Victoria (AU); John Berg, Victoria (AU); Michael Eric Schenberg, Victoria (AU)

(73) Assignee: Teleflex Life Sciences Unlimited Company, Hamilton (BM)

( * ) Notice: Subject to any disclaimer, the term of this patent is extended or adjusted under 35 U.S.C. 154(b) by 181 days.

(21) Appl. No.: 13/981,829

(22) PCT Filed: Feb. 2, 2012

(86) PCT No.: PCT/AU2012/000092
§ 371 (c)(1),
(2), (4) Date: Oct. 14, 2013

(87) PCT Pub. No.: WO2012/103589
PCT Pub. Date: Aug. 9, 2012

(65) Prior Publication Data
US 2014/0034060 A1 Feb. 6, 2014

(30) Foreign Application Priority Data
Feb. 2, 2011 (AU) ................................ 2011900332

(51) Int. Cl.
*A61M 16/04* (2006.01)

(52) U.S. Cl.
CPC ............................... *A61M 16/0434* (2013.01)

(58) Field of Classification Search
CPC .............. A61M 16/04; A61M 16/0488; A61M 16/0434; A61M 16/0486; A61M 16/00; A61M 16/0465; A61M 16/0479; A61M 16/0484; A61M 39/00; A61M 16/0409
USPC .................................................... 128/207.14
See application file for complete search history.

(56) References Cited

U.S. PATENT DOCUMENTS

| | | | |
|---|---|---|---|
| 2,096,831 A | 10/1937 | Wappler | |
| 2,252,874 A | 8/1941 | Vischer | |
| 2,839,788 A | 6/1958 | Dembiak | |
| 2,862,498 A | 12/1958 | Weekes | |
| 3,124,959 A | 3/1964 | Pall et al. | |
| 3,529,596 A | 9/1970 | Garner | |
| 3,554,673 A | 1/1971 | Schwartz et al. | |

(Continued)

FOREIGN PATENT DOCUMENTS

| | | | |
|---|---|---|---|
| AU | 2004 260 552 A1 | 2/2005 | |
| CA | 2012750 | 9/1990 | |

(Continued)

OTHER PUBLICATIONS

PCT/AU2012/000092 International Search Report dated Mar. 7, 2012.

(Continued)

*Primary Examiner* — Bradley H Philips
*Assistant Examiner* — Victoria Murphy
(74) *Attorney, Agent, or Firm* — Knobbe, Martens, Olson & Bear, LLP (57) ABSTRACT

An artificial airway including an airway tube having proximal and distal ends and a mask mounted at the distal end of the airway tube characterized in that the airway tube includes a curved portion adjacent to its distal end and a straight portion extending from the curved portion to the proximal end of the airway tube and the curved portion is more rigid than the straight portion.

16 Claims, 5 Drawing Sheets

(56) References Cited

U.S. PATENT DOCUMENTS

| | | |
|---|---|---|
| 3,683,908 A | 8/1972 | Michael et al. |
| 3,794,036 A | 2/1974 | Carroll |
| 3,931,822 A | 1/1976 | Marici |
| 4,056,104 A | 11/1977 | Jaffe |
| 4,067,329 A | 1/1978 | Winicki et al. |
| 4,096,759 A | 6/1978 | Desor |
| 4,104,357 A | 8/1978 | Blair |
| 4,116,201 A | 9/1978 | Shah |
| 4,134,407 A | 1/1979 | Elam |
| 4,159,722 A | 7/1979 | Walker |
| 4,178,938 A | 12/1979 | Au et al. |
| 4,178,940 A | 12/1979 | Au et al. |
| 4,231,365 A | 11/1980 | Scarberry |
| 4,256,099 A | 3/1981 | Dryden |
| 4,285,340 A | 8/1981 | Gezari et al. |
| 4,351,330 A | 9/1982 | Scarberry |
| 4,445,366 A | 5/1984 | Gray |
| 4,446,864 A | 5/1984 | Watson et al. |
| 4,453,545 A | 6/1984 | Inoue |
| 4,471,775 A | 9/1984 | Clair et al. |
| 4,501,273 A | 2/1985 | McGinnis |
| 4,509,514 A | 4/1985 | Brain et al. |
| 4,510,273 A | 4/1985 | Miura et al. |
| 4,526,196 A | 7/1985 | Pistillo |
| 4,531,330 A | 7/1985 | Phillips |
| 4,553,540 A | 11/1985 | Straith |
| 4,583,917 A | 4/1986 | Shah |
| 4,617,015 A | 10/1986 | Foltz |
| 4,630,606 A | 12/1986 | Weerda et al. |
| 4,654,643 A | 3/1987 | Meisenheimer, Jr. |
| 4,689,041 A | 8/1987 | Corday et al. |
| 4,700,700 A | 10/1987 | Eliachar |
| 4,770,170 A | 9/1988 | Sato et al. |
| 4,793,327 A | 12/1988 | Frankel |
| 4,798,597 A | 1/1989 | Vaillancourt |
| 4,809,589 A | 3/1989 | Bertrand |
| 4,825,862 A | 5/1989 | Sato et al. |
| 4,832,020 A | 5/1989 | Augustine |
| 4,850,349 A | 7/1989 | Farahany |
| 4,856,510 A | 8/1989 | Kowalewski et al. |
| 4,872,483 A | 10/1989 | Shah |
| 4,924,862 A | 5/1990 | Levinson |
| 4,953,547 A | 9/1990 | Poolf, Jr. |
| 4,972,963 A | 11/1990 | Guarriello et al. |
| 4,981,470 A | 1/1991 | Bombeck, IV |
| 4,995,388 A | 2/1991 | Brain |
| 5,038,766 A | 8/1991 | Parker |
| 5,042,469 A | 8/1991 | Augustine |
| 5,042,470 A | 8/1991 | Smith |
| 5,060,647 A | 10/1991 | Alessi |
| 5,067,496 A | 11/1991 | Eisele |
| 5,203,320 A | 4/1993 | Augustine |
| 5,218,970 A | 6/1993 | Turnbull et al. |
| 5,235,973 A | 8/1993 | Levinson |
| 5,237,988 A | 8/1993 | McNeese |
| 5,241,325 A | 8/1993 | Nguyen et al. |
| 5,241,956 A | 9/1993 | Brain et al. |
| 5,249,571 A | 10/1993 | Brain et al. |
| 5,273,537 A | 12/1993 | Haskvitz et al. |
| 5,277,178 A | 1/1994 | Dingley et al. |
| 5,282,464 A | 2/1994 | Brain et al. |
| 5,297,547 A | 3/1994 | Brain et al. |
| 5,303,697 A | 4/1994 | Brain et al. |
| 5,305,743 A | 4/1994 | Brain |
| 5,311,861 A | 5/1994 | Miller et al. |
| 5,331,967 A | 7/1994 | Akerson et al. |
| 5,339,805 A | 8/1994 | Parker |
| 5,339,808 A | 8/1994 | Don Michael |
| 5,355,879 A | 10/1994 | Brain et al. |
| 5,361,753 A | 11/1994 | Pothmann et al. |
| 5,391,248 A | 2/1995 | Brain et al. |
| 5,400,771 A | 3/1995 | Pirak et al. |
| 5,421,325 A | 6/1995 | Cinberg et al. |
| 5,438,982 A | 8/1995 | MacIntyre |
| 5,452,715 A | 9/1995 | Boussignac et al. |
| 5,459,700 A | 10/1995 | Jacobs |
| 5,487,383 A | 1/1996 | Levinson |
| 5,529,582 A | 6/1996 | Fukuhara et al. |
| 5,546,935 A | 8/1996 | Champeau |
| 5,546,936 A | 8/1996 | Virag et al. |
| 5,551,420 A | 9/1996 | Lurie et al. |
| 5,554,673 A | 9/1996 | Shah |
| 5,557,049 A | 9/1996 | Ratner |
| 5,569,219 A | 10/1996 | Hakki et al. |
| 5,577,693 A | 11/1996 | Corn |
| 5,582,167 A | 12/1996 | Joseph |
| 5,584,290 A | 12/1996 | Brain et al. |
| 5,599,301 A | 2/1997 | Jacobs et al. |
| 5,623,921 A | 4/1997 | Kinsinger et al. |
| 5,626,151 A | 5/1997 | Linden |
| 5,632,271 A | 5/1997 | Brain et al. |
| RE35,531 E | 6/1997 | Callaghan et al. |
| 5,653,229 A | 8/1997 | Greenberg |
| 5,655,528 A | 8/1997 | Pagan et al. |
| 5,682,880 A | 11/1997 | Brain et al. |
| 5,692,498 A | 12/1997 | Lurie et al. |
| 5,694,929 A | 12/1997 | Christopher |
| 5,711,293 A | 1/1998 | Brain et al. |
| 5,738,094 A | 4/1998 | Hoftman |
| 5,743,254 A | 4/1998 | Parker |
| 5,743,258 A | 4/1998 | Sato et al. |
| 5,746,202 A | 5/1998 | Pagan et al. |
| 5,771,889 A | 6/1998 | Pagan et al. |
| 5,778,872 A | 7/1998 | Fukunaga et al. |
| 5,791,341 A | 8/1998 | Bullard |
| 5,794,617 A | 8/1998 | Brunell et al. |
| 5,816,240 A | 10/1998 | Komesaroff |
| 5,819,723 A | 10/1998 | Joseph |
| 5,832,916 A | 11/1998 | Lundberg et al. |
| 5,850,832 A | 12/1998 | Chu |
| 5,855,203 A | 1/1999 | Matter |
| 5,856,510 A | 1/1999 | Meng et al. |
| 5,860,418 A | 1/1999 | Lundberg et al. |
| 5,865,176 A | 2/1999 | O'Neil et al. |
| 5,878,745 A | 3/1999 | Brain et al. |
| 5,881,726 A | 3/1999 | Neame |
| 5,893,891 A | 4/1999 | Zahedi et al. |
| 5,896,858 A | 4/1999 | Brain |
| 5,915,383 A | 6/1999 | Pagan |
| 5,921,239 A | 7/1999 | McCall et al. |
| 5,924,862 A | 7/1999 | White |
| 5,935,084 A | 8/1999 | Southworth |
| 5,937,860 A | 8/1999 | Cook |
| 5,957,133 A | 9/1999 | Hart |
| 5,979,445 A | 11/1999 | Neame et al. |
| 5,983,891 A | 11/1999 | Fukunaga |
| 5,983,896 A | 11/1999 | Fukunaga et al. |
| 5,983,897 A | 11/1999 | Pagan |
| 5,988,167 A | 11/1999 | Kamen |
| 5,996,582 A | 12/1999 | Turnbull |
| 6,003,510 A | 12/1999 | Anunta |
| 6,003,511 A | 12/1999 | Fukunaga et al. |
| 6,003,514 A | 12/1999 | Pagan |
| 6,012,452 A | 1/2000 | Pagan |
| 6,021,779 A | 2/2000 | Pagan |
| 6,050,264 A | 4/2000 | Greenfield |
| 6,062,219 A | 5/2000 | Lurie et al. |
| 6,070,581 A | 6/2000 | Augustine et al. |
| 6,079,409 A | 6/2000 | Brain |
| D429,811 S | 8/2000 | Bermudez et al. |
| 6,095,114 A | 8/2000 | Pagan |
| 6,098,621 A | 8/2000 | Esnouf et al. |
| 6,110,143 A | 8/2000 | Kamen |
| 6,116,243 A | 9/2000 | Pagan |
| 6,119,695 A | 9/2000 | Augustine et al. |
| 6,131,571 A | 10/2000 | Lampotang et al. |
| 6,149,603 A | 11/2000 | Parker |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald et al. |

(56) References Cited

U.S. PATENT DOCUMENTS

| | | |
|---|---|---|
| 6,315,739 B1 | 11/2001 | Merilainen et al. |
| 6,338,343 B1 | 1/2002 | Augustine et al. |
| 6,352,077 B1 | 3/2002 | Shah |
| 6,386,199 B1 | 5/2002 | Alfery |
| 6,390,093 B1 | 5/2002 | Mongeon |
| 6,422,239 B1 | 7/2002 | Cook |
| 6,427,686 B2 | 8/2002 | Augustine et al. |
| 6,439,232 B1 | 8/2002 | Brain |
| 6,450,164 B1 | 9/2002 | Banner et al. |
| 6,508,250 B1 | 1/2003 | Esnouf |
| 6,511,922 B2 | 1/2003 | Krishnaraj et al. |
| 6,546,931 B2 | 4/2003 | Lin et al. |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |
| 6,737,345 B1 | 5/2004 | Lin et al. |
| 6,766,801 B1 | 7/2004 | Wright |
| 7,004,169 B2 | 2/2006 | Brain et al. |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,066,178 B2 * | 6/2006 | Gunaratnam ......... A61M 16/06 128/206.21 |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain et al. |
| 7,159,589 B2 | 1/2007 | Brain |
| 7,383,736 B2 | 6/2008 | Esnouf |
| 7,566,658 B2 | 7/2009 | Keum |
| 7,650,886 B1 * | 1/2010 | Keller ............... A61M 16/0488 128/207.14 |
| 7,694,682 B2 | 4/2010 | Petersen et al. |
| 7,895,497 B2 | 2/2011 | Pisek et al. |
| 8,013,423 B2 | 9/2011 | Keum |
| 8,033,176 B2 | 10/2011 | Esnouf |
| 8,358,011 B1 | 1/2013 | Colburn et al. |
| 8,716,871 B2 | 5/2014 | Tseng et al. |
| 9,528,897 B2 | 12/2016 | Esnouf et al. |
| 2002/0026178 A1 | 2/2002 | Ouchi |
| 2003/0000534 A1 | 1/2003 | Alfery |
| 2003/0037790 A1 | 2/2003 | Brain |
| 2003/0051734 A1 | 3/2003 | Brain |
| 2003/0101998 A1 | 6/2003 | Zocca et al. |
| 2003/0131845 A1 | 7/2003 | Lin |
| 2003/0172925 A1 | 9/2003 | Zocca et al. |
| 2003/0172935 A1 | 9/2003 | Miller |
| 2004/0020491 A1 | 2/2004 | Fortuna |
| 2004/0089307 A1 | 5/2004 | Brain |
| 2005/0066975 A1 | 3/2005 | Brain |
| 2005/0081861 A1 * | 4/2005 | Nasir ................ A61M 16/04 128/207.14 |
| 2005/0139220 A1 | 6/2005 | Christopher |
| 2005/0178388 A1 | 8/2005 | Kuo |
| 2005/0274383 A1 | 12/2005 | Brain |
| 2006/0124132 A1 | 6/2006 | Brain |
| 2006/0180156 A1 | 8/2006 | Baska |
| 2006/0201516 A1 | 9/2006 | Petersen et al. |
| 2006/0254596 A1 | 11/2006 | Brain |
| 2007/0240722 A1 | 10/2007 | Kessler |
| 2008/0041392 A1 | 2/2008 | Cook |
| 2008/0048332 A1 | 2/2008 | Park |
| 2008/0142017 A1 | 6/2008 | Brain |
| 2008/0173981 A1 | 7/2008 | Chinthakindi et al. |
| 2008/0276936 A1 | 11/2008 | Cook |
| 2009/0102052 A1 | 4/2009 | Ryu |
| 2009/0139524 A1 | 6/2009 | Esnouf |
| 2009/0212439 A1 | 8/2009 | Farooq et al. |
| 2009/0261475 A1 | 10/2009 | Keum |
| 2009/0320853 A1 * | 12/2009 | Kenowski ......... A61M 16/0443 128/207.14 |
| 2010/0059061 A1 | 3/2010 | Brain |
| 2010/0089393 A1 | 4/2010 | Brain |
| 2010/0216123 A1 | 8/2010 | Hirai et al. |
| 2011/0024866 A1 | 2/2011 | Tseng et al. |
| 2011/0226256 A1 | 9/2011 | Dubach |
| 2011/0245805 A1 | 10/2011 | Swinehart et al. |
| 2011/0256546 A1 | 10/2011 | Morris et al. |
| 2011/0281432 A1 | 11/2011 | Farooq et al. |
| 2012/0048279 A1 | 7/2012 | Esnouf |
| 2012/0174929 A1 | 7/2012 | Esnouf |
| 2012/0186510 A1 | 7/2012 | Esnouf |
| 2014/0087380 A1 | 3/2014 | Kurose |
| 2017/0146419 A1 | 5/2017 | Esnouf |

FOREIGN PATENT DOCUMENTS

| | | | |
|---|---|---|---|
| CA | 2067782 | 5/1991 | |
| CA | 2141167 A1 | 7/1995 | |
| CN | 2579352 Y | 10/2003 | |
| CN | 1863568 A | 11/2006 | |
| CN | 2882657 Y | 3/2007 | |
| CN | 201516220 U | 6/2010 | |
| CN | 201684261 U | 12/2010 | |
| CN | 101991898 A | 3/2011 | |
| CN | 103221087 B | 7/2013 | |
| DE | 2945662 A1 | 5/1981 | |
| DE | 100 42 172 A1 | 4/2001 | |
| EP | 0 294 200 B1 | 12/1988 | |
| EP | 0 389 272 A2 | 9/1990 | |
| EP | 0 402 872 A1 | 12/1990 | |
| EP | 0 580 385 A1 | 1/1994 | |
| EP | 0 712 638 A1 | 5/1996 | |
| EP | 0 732 116 A2 | 9/1996 | |
| EP | 0 796 631 A2 | 9/1997 | |
| EP | 0 842 672 A2 | 5/1998 | |
| EP | 0 845 276 A2 | 6/1998 | |
| EP | 0 865 798 A2 | 9/1998 | |
| EP | 0 922 465 A2 | 6/1999 | |
| EP | 0 935 971 A2 | 8/1999 | |
| EP | 1 119 386 B1 | 8/2001 | |
| EP | 1 125 595 A1 | 8/2001 | |
| EP | 1 800 706 A1 | 6/2007 | |
| EP | 1800706 A1 * | 6/2007 | ............ A61M 16/04 |
| GB | 1 529 190 A | 10/1978 | |
| GB | 2 111 394 A | 7/1983 | |
| GB | 2 205 499 A | 12/1988 | |
| GB | 2 298 797 A | 9/1996 | |
| GB | 2 317 342 A | 3/1998 | |
| GB | 2 317 830 A | 4/1998 | |
| GB | 2 318 735 A | 5/1998 | |
| GB | 2 319 478 A | 5/1998 | |
| GB | 2 321 854 A | 8/1998 | |
| GB | 2 323 289 A | 9/1998 | |
| GB | 2 323 290 A | 9/1998 | |
| GB | 2 323 291 A | 9/1998 | |
| GB | 2 323 292 A | 9/1998 | |
| GB | 2 359 996 A | 9/2001 | |
| GB | 2 405 588 A | 3/2005 | |
| GB | 2 436 294 | 9/2007 | |
| GB | 2454199 A | 5/2009 | |
| GB | 2436294 B | 12/2009 | |
| JP | H03-39169 A | 2/1991 | |
| JP | H08-547 A | 1/1996 | |
| JP | H10-118182 A | 5/1998 | |
| JP | H10-179745 A | 7/1998 | |
| JP | H10-216233 A | 8/1998 | |
| JP | H10-263086 A | 10/1998 | |
| JP | H10-277156 A | 10/1998 | |
| JP | H10-314308 A | 12/1998 | |
| JP | H10-323391 A | 12/1998 | |
| JP | H10-328303 A | 12/1998 | |
| JP | H11-128349 A | 5/1999 | |
| JP | H11-192304 A | 7/1999 | |
| JP | H11-206885 A | 8/1999 | |
| JP | P2000-152995 A | 6/2000 | |
| JP | P2003-528701 A | 9/2003 | |
| JP | 2008-526393 A | 7/2008 | |
| TW | 200706196 A | 2/2007 | |
| WO | WO-91/03207 A1 | 3/1991 | |
| WO | WO-91/07201 A1 | 5/1991 | |
| WO | WO-91/12845 A1 | 9/1991 | |

(56) References Cited

FOREIGN PATENT DOCUMENTS

| | | |
|---|---|---|
| WO | WO-92/13587 A1 | 8/1992 |
| WO | WO-94/02191 A1 | 2/1994 |
| WO | WO-95/33506 A1 | 12/1995 |
| WO | WO-97/12640 A1 | 4/1997 |
| WO | WO-97/12641 A1 | 4/1997 |
| WO | WO-98/16273 A1 | 4/1998 |
| WO | WO-99/06093 A1 | 2/1999 |
| WO | WO-00/09189 A1 | 2/2000 |
| WO | WO-00/20062 A2 | 4/2000 |
| WO | WO-00/22985 A1 | 4/2000 |
| WO | WO-00/23135 A1 | 4/2000 |
| WO | WO-00/61212 A1 | 10/2000 |
| WO | WO-01/74431 A2 | 10/2001 |
| WO | WO-02/32490 A2 | 4/2002 |
| WO | WO-2004/030527 A1 | 4/2004 |
| WO | WO-2004/089453 A2 | 10/2004 |
| WO | WO-2005/023350 A1 | 3/2005 |
| WO | WO-2005/058394 A1 | 6/2005 |
| WO | WO-2006/026237 A1 | 3/2006 |
| WO | WO 06/037626 | 4/2006 |
| WO | WO 06/125986 | 11/2006 |
| WO | WO-2006/125989 A1 | 11/2006 |
| WO | WO 07/131267 | 11/2007 |
| WO | WO-2008/001724 A1 | 1/2008 |
| WO | WO 2008/146893 A1 | 12/2008 |
| WO | WO 09/156949 | 12/2009 |
| WO | WO 10/060224 | 6/2010 |
| WO | WO 2011/003135 A1 | 1/2011 |
| WO | WO-2012/061869 A1 | 5/2012 |
| WO | WO 13/066195 | 5/2013 |

OTHER PUBLICATIONS

Abdelatti, M.O., "A Cuff Pressure Controller for Tracheal Tubes and Laryngeal Mask Airways," Anaesthesia, 1999, 54, pp. 981-986, Blackwell Science Ltd.
Benumof, "Laryngeal Mask Airway and the ASA Difficult Airway Algorithm," Anesthesiology, 1996: 84.686-99.
Benumof, "Management of the Difficult Adult Airway with Special Emphasis on Awake Tracheal Intubation." Anesthesiology 75:1087-1110, 1991.
Bernhard et al. "Adjustment of Intracuff Pressure to Prevent Aspiration," Anesthesiology, 50: 363-366, 1979.
Bernhard et al., "Physical Characteristics of and Rates of Nitrous Oxide Diffusion into Tracheal Tube Cuffs," Anesthesiology 48:413-417, 1978.
Brain et al., "A New Laryngeal Mask Prototype," Anaesthesia, 1995, vol. 50, pp. 42-48.
Brain et al., "The Laryngeal Mask Airway, Development and Preliminary Trials of a New Type of Airway," Anaesthesia, 1985, vol. 40, pp. 356-361.
Brain, "The Laryngeal Mask—A New Concept in Airway Management," Br. J. Anaesth. (1983), 55, 801-805.
Brain, "The Laryngeal Mask Airway—A Possible New Solution to Airway Problems in the Emergency Situation," Archives of Emergency Medicine, 1984, 1, 229-232.
Brain, "Three Cases of Difficult Intubation Overcome by the Laryngeal Mask Airway," Anaesthesia, 1985, vol. 40, pp. 353-355.
Brimacombe, "The Split Laryngeal Mask Airway," Anaesthesia, Jul. 1993; 48(7):039.
Brodrick et al, "The Laryngeal Mask Airway, A Study of 100 Patients During Spontaneous Breathing," Anaesthesia, 1989, vol. 44, pp. 238-241.
Burgard et al, "The Effect of Laryngeal Mask Cuff Pressure on Postoperative Sore Throat Incidence," Journal of Clinical Anesthesia 8:198-201, 1996.
Caplan et al, "Adverse Respiratory Events in Anesthesia: A Closed Claims Analysis," Anesthesiology 72:828-833, 1990.
Craven, "Prevention of Hospital-Acquired Pneumonia: Measuring Effect in Ounces, Pounds, and Tons," Annals of Internal Medicine, vol. 122, No. 2, pp. 229-231 (Feb. 1, 1995).
Cuff-Pressure Control CDR 2000, Technical Data, 4 pages, Manufacturer ESW-EXTEL Systems Wedel, Gesellschaft fur Ausrustung mbH, 2000.
Davies et al, "Laryngeal Mask Airway and Tracheal Tube Insertion by Unskilled Personnel," The Lancet, 1990; 336:977-79.
de Mello et al, "The Use of the Laryngeal Mask Airway in Primary Anaesthesia," Anaesthesia. Sep. 1990;45(9):793-4.
Doyle et al., "Intraoperative Awareness: A Continuing Clinical Problem," Educational Synopses in Anesthesiology and Critical care Medicine, The Online Journal of Anesthesiology vol. 3 No. 6, 8 pages, Jun. 1996.
Engbers, "Practical use of Diprifusor" Systems, Anaesthesia, 1998, 53, Supplement 1, pp. 28-34.
Eriksson et al, "Functional Assessment of the Pharynx at Rest and During Swallowing in Partially Paralyzed Humans," Anesthesiology vol. 87, No. 5, pp. 1035-1042, Nov. 1997.
Glen, "The Development of 'Diprifusor': a TCI System for Propofol," Anaesthesia, 1998, 53, Supplement 1, pp. 13-21.
Gray et al, "Development of the Technology for 'Diprifusor' TCI Systems," Anaesthesia, 1998, Supplement 1, pp. 22-27.
Heath, "Endotracheal Intubation Through the Laryngeal Mask—Helpful When Laryngoscopy is Difficult or Dangerous," European Journal of Anaesthesiology, 1991, Supplement 4, 41-45.
Hickey et al, "Cardiovascular Response to Insertion of Brain's Laryngeal Mask," Anaesthesia, 1990, vol. 45, pp. 629-633.
Inomata et al, "Transient Bilateral Vocal Cord Paralysis After Insertion of a Laryngeal Mask Airway," Anaesthesiology,82;787-788, 1995.
International Search Report in PCT/GB2006/001913 dated Aug. 26, 2006.
Jacobson et al, "A Study of Intracuff Pressure Measurements, Trends and Behaviour in Patients During Prolonged Periods of Tracheal Intubation," Br. J. Anaesth. (1981), 53, 97-101.
Kambic et al, "Intubation Lesions of the Larynx," Br. J. Anaesth. (1978), 50, 587-590.
Kangas, "Neurometric Assessment of Adequacy of Intraoperative Anesthetic," Pacific Northwest National Laboratory, retrieved May 13, 2008, 3 pages.
Kapila, et al., "Proceedings of the Anaesthetic Research Society, Leeds Meeting, Mar. 31-Apr. 1, 1995," British Journal of Anaesthesia, 1995, 75:228P-229P.
Lindholm, "Methods," ACTA Anaesthesiologica Scandinavica, Prolonged Endotracheal Intubation, Chapter III, pp. 32-46 (1969).
Majumder et al, "Bilateral Lingual Nerve Injury Following the Use of the Laryngeal Mask Airway," Anaesthesia, 1998, 53, 169-191.
Martin, Patentability of Methods of Medical Treatment: A Comparative Study, J. Pat & Trademark Off. Soc'y, pp. 381-423, 2000.
Merriam Webster's Collegiate Dictionary, $10^{th}$ Ed., 1997, pp. 254 and 1029, definitions of "Convex" and "Saddle".
Miller, "A Pressure Regulator for the Cuff of the Tracheal Tube," Anaesthesia, 1992, vol. 47, pp. 594-596.
Muthuswamy et al., "The Use of Fuzzy Integrals and Bispectral Analysis of the Electroencephalogram to Predict Movement Under Anesthesia," Transactions on Biomedical Engineering, vol. 46, No. 3, Mar. 1999.
Nagai et al., "Unilateral hypoglossal nerve paralysis following use of the laryngeal mask airway," Anaesthesia, vol. 49, pp. 603-604, 1994.
Observations by a third party concerning European Patent Application No. 99 947 765.6 dated Jan. 18, 2005, 4 pages.
Patel et al., "Tracheal Tube Cuff Pressure," Anaesthesia, vol. 39, pp. 862-864, 1984, 3 pages.
Pennant et al., "Comparison of the Endotracheal Tube and Laryngeal Mask in Airway Management by Paramedical Personnel," Anesth. Analog, pp. 531-534, 1992.
Pippin et al., "Long-term tracheal intubation practice in the United Kingdom," Anaesthesia, vol. 38, pp. 791-795, 1983.
Raeder et al., "Tracheal tube cuff pressures," Anaesthesia, vol. 40, pp. 444-447, 1985.
Response to Complaint in *LMA Deutschland Gmbh v. AMBU (Deutschland) Gmbh*, dated Feb. 10, 2006.

(56) References Cited

OTHER PUBLICATIONS

Rieger et al., "Intracuff Pressures Do Not Predict Laryngopharyngeal Discomfort after Use of the Laryngeal Mask Airway," Anesthesiology, vol. 87, No. 1, Jul. 1997, pp. 63-67.
Seegobin et al., "Endotracheal cuff pressure and tracheal mucosal blood flow: endoscopic study of effects of four volume cuffs," British Medical Journal, vol. 288, Mar. 1984, pp. 965-968.
Willis, et al., "Tracheal tube cuff pressure," Anaesthesia, vol. 43, pp. 312-314, 1988.
Worthington, et al., "Proceedings of the Anaesthetic Research Society, Leeds Meeting, Mar. 31-Apr. 1, 1995." British Journal of Anaesthesia, 1995, 75:228P.
Wynn et al., "Tongue Cyanosis after Laryngeal Mask Airway Insertion," Anesthesiology, vol. 80, No. 6, Jun. 1994.
Office Action dated Sep. 15, 2014 in U.S. Appl. No. 13/254,594 (US 2012/0048279).
Office Action dated May 20, 2015 in U.S. Appl. No. 13/254,594 (US 2012/0048279).
Office Action dated on Jan. 13, 2016 in U.S. Appl. No. 13/254,594 (US 2012/0048279).
Office Action dated Mar. 28, 2013 in U.S. Appl. No. 13/397,488 (now U.S. Pat. No. 8,716,871).
Office Action dated Jul. 19, 2013 in U.S. Appl. No. 13/397,488 (now U.S. Pat. No. 8,716,871).
Notice of Allowance dated Dec. 16, 2013 in U.S. Appl. No. 13/397,488 (now U.S. Pat. No. 8,716,871).
Office Action dated Oct. 17, 2012 in U.S. Appl. No. 12/518,776 (US 2010/0089393).
Office Action dated Apr. 24, 2013 in U.S. Appl. No. 12/518,776 (US 2010/0089393).
Office Action dated Mar. 17, 2014 in U.S. Appl. No. 12/518,776 (US 2010/0089393).
Office Action dated Jul. 2, 2014 in U.S. Appl. No. 12/518,776 (US 2010/0089393).
Office Action dated Nov. 26, 2014 in U.S. Appl. No. 12/518,776 (US 2010/0089393).
Office Action dated Apr. 15, 2015 in U.S. Appl. No. 12/518,776 (US 2010/0089393).
Office Action dated Oct. 2, 2015 in U.S. Appl. No. 12/518,776 (US 2010/0089393).
Office Action dated May 25, 2012 in U.S. Appl. No. 11/915,558 (US 2010/0059061).
Office Action dated Feb. 14, 2013 in U.S. Appl. No. 11/915,558 (US 2010/0059061).
Office Action dated May 24, 2013 in U.S. Appl. No. 11/915,558 (US 2010/0059061).
Office Action dated Oct. 23, 2013 in U.S. Appl. No. 11/915,558 (US 2010/0059061).
Office Action dated Jul. 17, 2014 in U.S. Appl. No. 11/915,558 (US 2010/0059061).
Office Action dated Dec. 16, 2014 in U.S. Appl. No. 11/915,558 (US 2010/0059061).
Office Action dated Apr. 8, 2015 in U.S. Appl. No. 11/915,558 (US 2010/0059061).
Office Action dated Jan. 13, 2016 in U.S. Appl. No. 11/915,558 (US 2010/0059061).
Office Action dated May 13, 2015 in U.S. Appl. No. 14/029,831 (US 2014/0087380).
Office Action dated Jul. 22, 2015 in U.S. Appl. No. 14/029,831 (US 2014/0087380).
Notice of Allowance dated Dec. 11, 201 in U.S. Appl. No. 14/029,831 (US 2014/0087380).
Office Action dated Jul. 3, 2014 in U.S. Appl. No. 13/388,864 (US 2012/0186510).
Office Action dated Feb. 23, 2015 in U.S. Appl. No. 13/388,864 (US 2012/0186510).
Office Action dated Oct. 21, 2015 in U.S. Appl. No. 13/388,864 (US 2012/0186510).
International Search Report in PCT/AU2010/001024 dated Oct. 11, 2010.
Brimacombe, "Laryngeal Mask Anesthesia—Principles and Practice," $2^{nd}$ edition, Chapters 1-22, Appendices A-C, Saunders/Elsevier Limited, 2005.
Notice of Allowance dated Apr. 13, 2016 in U.S. Appl. No. 13/388,864 (US 2012/0186510).
Notice of Allowance dated May 4, 2016 in U.S. Appl. No. 11/915,558 (US 2010/0059061).
Notice of Allowance dated May 4, 2016 in U.S. Appl. No. 12/518,776 (US 2010/0089393).
Notice of Allowance dated Jun. 8, 2016 in U.S. Appl. No. 11/915,558 (US 2010/0059061).
Notice of Allowance dated Jul. 1, 2016 in U.S. Appl. No. 12/518,776 (US 2010/0089393).
Notice of Allowance dated Aug. 12, 2016 in U.S. Appl. No. 11/915,558 (US 2010/0059061).
Office Action dated Nov. 27, 2017 in U.S. Appl. No. 15/361,655 (US 2017/0146419).
Office Action dated Apr. 14, 2016 in U.S. Appl. No. 13/254,594 (US 2012/0048279).
Office Action dated Jun. 20, 2017 in U.S. Appl. No. 13/254,594 (US 2012/0048279).
Office Action dated Aug. 22, 2013 in U.S. Appl. No. 12/518,776 (US 2010/0089393).
Office Action dated Nov. 22, 2017 in U.S. Appl. No. 13/254,594 (US 2012/0048279).

* cited by examiner

$$I = \frac{\pi}{64}(D_1^4 - D_{1i}^4)$$

FIG. 4

$$d = \frac{PL^3}{3EI}$$

ARTIFICIAL AIRWAY

This invention relates to an artificial airway of the type which is normally used in surgery.

There are many forms of artificial airways available. One common form has a hollow tube which is coupled to a mask, which frequently includes an inflatable cuff, which when inserted covers the laryngeal opening and provides an effective seal around the laryngeal opening. Anaesthetic gases can then be supplied through the hollow tube to the patient.

Normally the tube is moulded from plastics material and is flexible at least to some extent. Some tubes are relatively rigid whereas others are much more flexible or floppy and are such that they would bend under their own weight.

The essentially rigid tubes are capable of maintaining their shape during the insertion of the mask and can be used as a handle during this process. Some are gently curved, but capable of further bending to conform to shape required to sit against the hard palate and posterior pharynx. Other airway tubes are preformed with a curve of 60 to 90 degrees to more closely match this anatomical angle.

The more flexible tubes are generally made from a soft plastics or elastomeric material such as silicone rubber or PVC that allow the tubing to be easily bent or floppy. The tube is generally reinforced with a spiral wire in order to prevent occlusion by sharp bending. Furthermore, the wire reinforcement prevents crushing and occlusion should a patient bite down upon the tube. The advantage of the flexible tubes is that they can be easily be manoeuvred after the airway is in place so as not to interfere with a surgeon working in the area of the head, neck or oral cavity. As such laryngeal mask airways with flexible tubes are popular with such specialities as head and neck surgery and ear, nose and throat surgery. A disadvantage of these tubes is that they are difficult to insert as the tube cannot be used as a handle because the tube tends to bend uncontrollably if any pressure is applied to it during the insertion process. The recommended technique for insertion of these airways is for the mask section of the airway to be grasped and inserted using (gloved) fingers. This is not popular with anaesthetists. Various introducers have been designed to avoid this requirement, but by and large have also proved to be unpopular.

The object of the invention is to avoid the disadvantages above.

Broadly speaking, the invention provides an artificial airway which has a composite tube which has characteristics of both rigid and flexible tubes.

More specifically, the invention provides an artificial airway including an airway tube having proximal and distal ends and a mask mounted at the distal end of the airway tube characterized in that the airway tube includes a curved portion adjacent to its distal end and a straight portion extending from the curved portion to the proximal end of the airway tube and the curved portion is more rigid than the straight portion.

Preferably the curved portion is moulded from first material which is less flexible than second material from which the straight portion is moulded.

Preferably the Shore A hardness of the first material is 40 to 50 and the Shore A hardness of the second material is 30 to 40.

Preferably the curved and straight portions are of annular cross-section.

Preferably the outer diameter of the curved portion is greater than that of the straight portion.

Preferably the outer diameter of the curved portion is in the range 15 to 17 mm.

Preferably the wall thickness of the curved portion is in the range 3 to 3.2 mm.

Preferably the outer diameter of the straight portion is in the range 11 to 13 mm.

Preferably the wall thickness of the straight portion is in the range 1.4 to 1.5 mm.

Preferably the straight portion includes a supporting spring to help prevent occlusion thereof.

Preferably the curved and straight portions are moulded separately and then joined together.

Preferably they are integrally moulded by co-moulding.

Preferably the modulus of elasticity of the curved portion is substantially greater than the modulus of elasticity of the straight portion.

Preferably, when straight samples of equal lengths are supported at one end and a lateral force is applied to the other end, the deflection of the sample of the curved portion is about 10 times that of the sample of the straight tube.

Preferably the modulus of elasticity of the sample of the curved tube is about 1.5 to 5 times greater than that of the straight tube. Preferably further the ratio is about 2.5.

The artificial airway of the invention has the advantage that it can be inserted in a similar manner to a rigid laryngeal mask. The user can grasp the relatively rigid curved portion and use it as a handle for inserting the mask. After insertion, the more flexible straight portion can be positioned in much the same way as the tube of known flexible laryngeal mask airways to allow good surgical access.

In addition, the mask of the airway of the invention is effectively stabilised once inserted because the curved portion is seated against the hard palate and the posterior pharynx and therefore it is much less likely to be inadvertently displaced as can sometimes happen with known devices which have a fully flexible tube.

The invention also provides an airway tube for an artificial airway, the airway tube having proximal and distal ends and, in use, a mask mounted at the distal end of the airway tube characterized in that the airway tube includes a curved portion adjacent to its distal end and a straight portion extending from the curved portion to the proximal end of the airway tube and the curved portion is more rigid than the straight portion.

Figure 1:
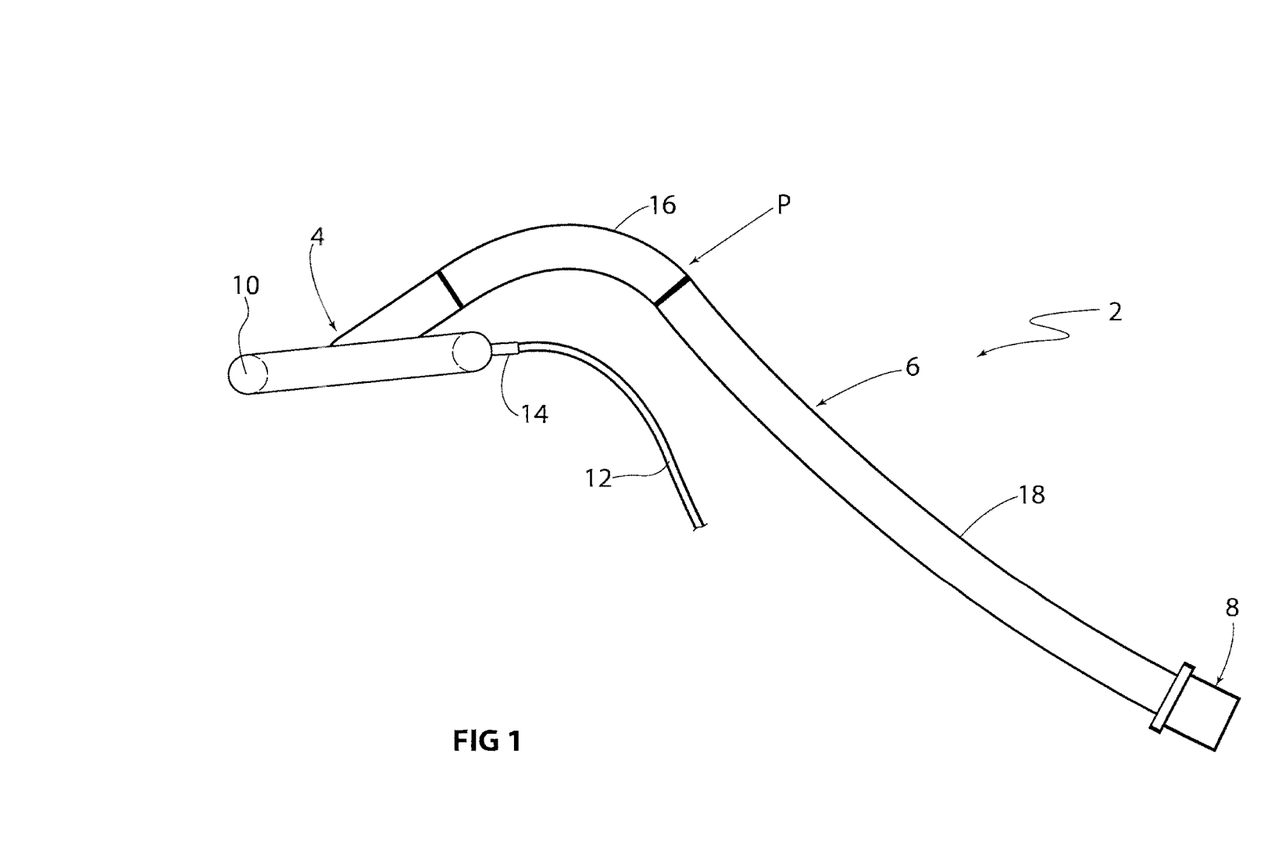
FIG. 1 is a schematic side view of a laryngeal mask constructed in accordance with the invention.
Figure 2:
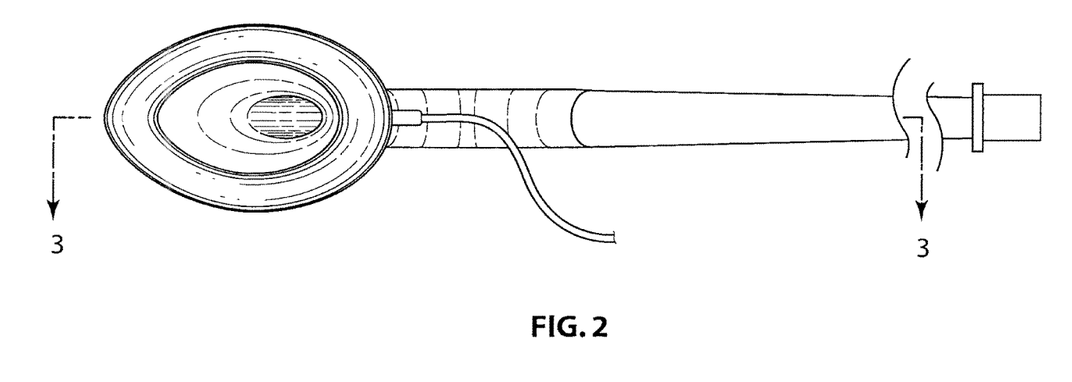
FIG. 2 is an underside view of the mask.

The invention will now be further described with reference to the accompanying drawings, in which:

FIG. 1 shows an artificial airway 2 constructed in accordance with the invention.

The airway includes a mask 4 and airway tube 6, the tube 6 being fitted with a male Leur connector 8 at its proximal end. The mask 4 includes an inflatable peripheral cuff 10 which is inflated in use by means of an inflation line 12 which opens to the interior of the cuff by means of a spigot 14. The mask 2 is preferably moulded from silicone rubber. The structure of the mask can be the same or similar to known masks and therefore need not be described in detail.

The airway tube 6 of the invention includes a curved portion 16 and a relatively straight portion 18. As will be described in more detail below, the curved portion 16 is moulded in such a way that it is much more rigid than the straight portion 18. In this specification the reference to the portion 18 as being straight means it is moulded so as to be linear or slightly curved. The flexibility of the portion 18 however is such that it can readily be resiliently deflected and the word straight in that context should be understood in that context.

Figure 3:
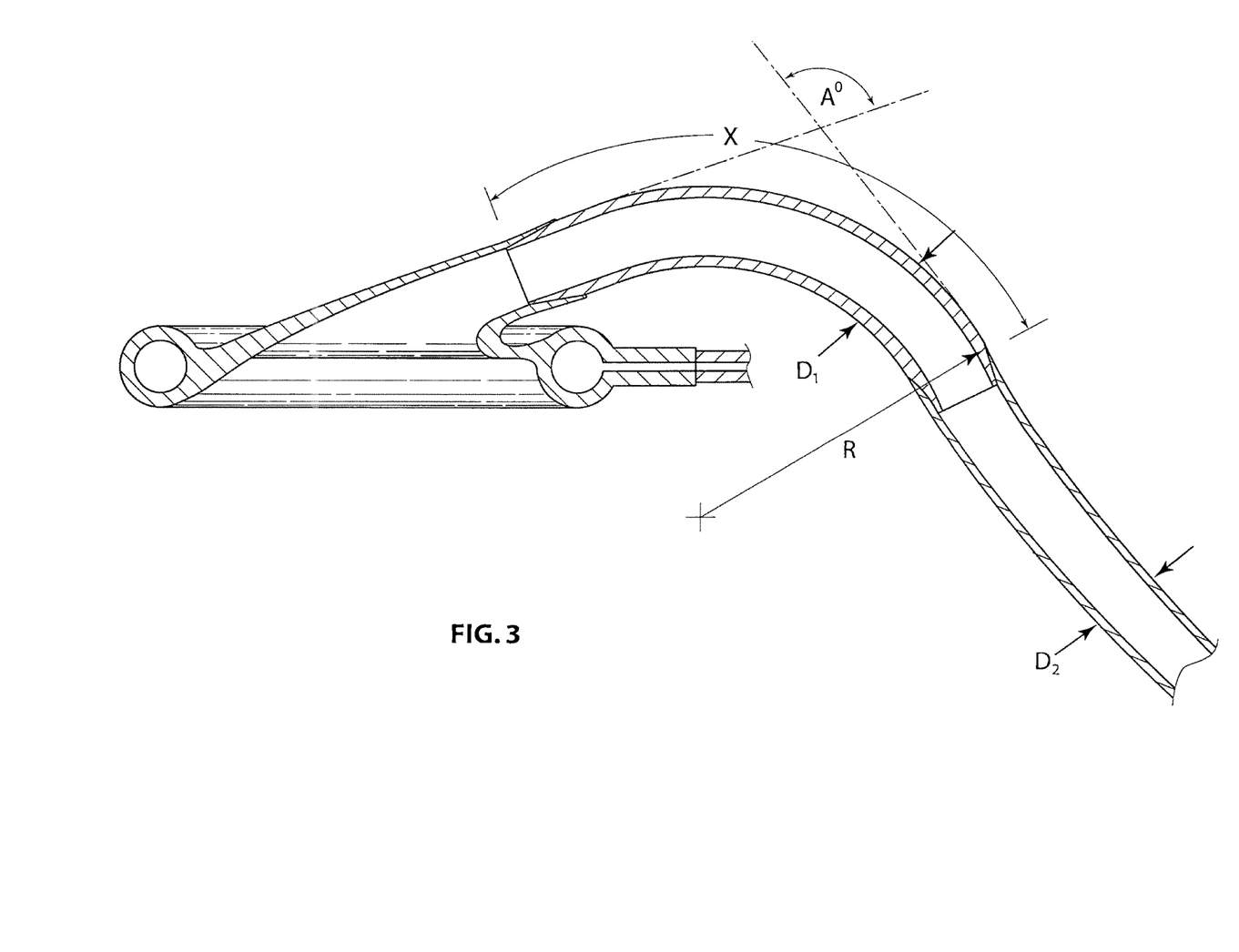
FIG. 3 is a schematic longitudinal cross-section along the line 3-3.

In one embodiment, the length X as shown in FIG. 3 of the curved portion 16 is about 80 mm whereas the length of the straight portion 18 can be 210 mm. Typically, the ratio of the lengths is about 1:3 but this can be varied in accordance with the size of the airway device.

The curved portion 16 is preferably moulded from silicone rubber or PVC and the straight portion 18 is preferably moulded from silicone rubber or PVC so that it is significantly more flexible than the portion 10. The straight portion 18 is preferably reinforced by a spiral wire (not shown). The techniques for providing the spiral wire support are known in the art and therefore need not be described. The material from which the curved portion 16 is moulded is preferably more rigid than the material which is used for moulding the straight portion 18. Typically the Shore hardness of the material for the rigid portion 16 is 40 to 50 A whereas that of the straight portion 18 is 30 to 40 A. Both the curved portion 16 and the straight portion 18 are preferably of circular inner and outer diameters. The wall thickness of the curved portion 16 is preferably greater than the wall thickness of the straight portion 18. Typically the wall thickness of the curved portion 16 is the range 3 to 3.2 mm whereas the wall thickness of the flexible tube is in the range 1.4 to 1.5 mm.

It is possible that the curved portion 16 and straight portion 18 could be integrally moulded from the same material and the differential wall thicknesses provides the difference in rigidity between these two parts of the tube.

It is preferred however that the curved portion 16 and straight portion 18 are separately moulded and then joined together by over-moulding, solvent welding, bonding or other techniques. As best seen in FIG. 3, the proximal end 20 of the curved portion 16 is somewhat tapered so that it can be inserted in the distal end 22 of the straight portion 18 so that the transition between the portion 16 and 18 is relatively smooth internally and externally.

It is also possible that the airway tube 6 could be integrally moulded by injecting harder material in that part of the mould which forms the curved portion 16 and softer material into that part of the mould which forms the straight portion 18 by using known co-moulding techniques.

Figure 4:
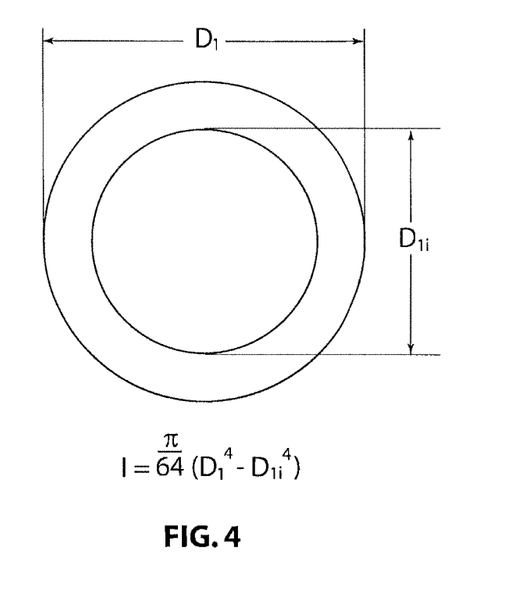
FIGS. 4 and 5 are diagrams useful in understanding the physical properties of the tube.

A prototype of the device 2 of the invention has been constructed and has been found to have desirable properties in that the curved portion 16 is much less susceptible to bending than the straight portion 18. An investigation of the deflection and modulus of elasticity for the curved portion 16 and straight portion 18 has been carried out. FIG. 4 shows a diagram which enables calculation of the moment of inertia I for a hollow tube where $D_1$ is the outer diameter and $D_1i$ is the inner diameter. The moment of inertia is given by: $I=(Pi \div 64) (D_1^4-D_{1i}^4)$.

$$I = \frac{\pi}{64}(D_1^4 - D_{1i}^4) \qquad \text{Equation 1}$$

For a typical curved portion 16, the outer diameter $D_1$ is say 16 mm whereas the inner diameter $D_{1i}$ is 9.8 mm. Using Equation 1 above, the moment of inertia I is $2.764 \times 10^{-9}$ m4.

Typically, for the straight portion 18, $D_1$ is 12 mm and $D_{1i}$ is 9.1 mm. Therefore using Equation 1 above, the moment of inertia I is $6.813 \times 10^{-10}$ m$^4$.

Figure 5:
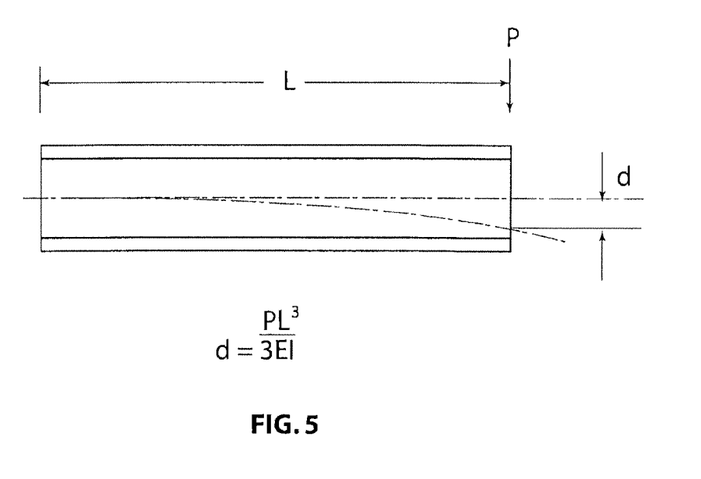

Sample lengths of the material, each 100 mm long for the curved portion 16 and straight portion 18 which were both initially straight were then clamped at one end and subjected to a transverse force applied to the other end in order to measure the deflection. In the deflection test, the free end was deflected by 5 mm. In the case of the rigid sample, the force required was 25 gms. In the case of the flexible sample, the force required was 2.5 gms. This illustrates that the straight portion 18 is much more susceptible to bending than the curved portion 16. From these deflection tests, it is possible to compute the approximate values for the modulus of elasticity for the straight samples of the curved and straight portions of the tube. The following equation can be used for this purpose:

$$d = \frac{PL^3}{3EI} \qquad \text{Equation 2}$$

where d is the deflection, P is the applied force, L is the length, E is the modulus of elasticity and I is the moment of inertia.

Using Equations 1 and 2 above, for the straight samples, the modulii of elasticity can be determined as follows as in Table 1 below:

TABLE 1

| | Force (g) | Outer D (m) | Inner D (m) | I (m4) | E (n/m2) | E (psi) |
|---|---|---|---|---|---|---|
| Straight Portion 18 | 2.5 | 0.012 | 0.0091 | 6.81259E−10 | 2399966.648 | 348.085734 |
| Curved Portion 16 | 25 | 0.016 | 0.0098 | 2.76422E−09 | 5914859.739 | 857.8778772 |

The ratio of the modulii is therefore about 2.5 for the prototype.

It will be appreciated that when the curved portion 16 itself (rather than a straight sample thereof) is subjected to a bending force such as a force P applied at its proximal end, as indicated by the letter P in FIG. 1 the force required for 5 mm of deflection is greater than for the straight sample. In one test on the prototype a force of about 65 gm was required to produce 5 mm deflection and therefore it will be understood that the modulus of elasticity for the curved portion 16 is at least 5 times that of the straight portion 18.

The airway device 2 can be made in different sizes for use with patients in different age categories. Table 2 below shows the nominal size S of the device 2 and the typical values for $RD_1$ and the length X, as shown in FIG. 3.

TABLE 2

| S | R mm | D₁ mm | X mm |
|---|------|-------|------|
| 3 | 50 | 15.6 | 80 |
| 4 | 54 | 15.6 | 90 |
| 5 | 65 | 16.8 | 100 |

The dimensions may be varied for larger or smaller sizes.

Figure 6:
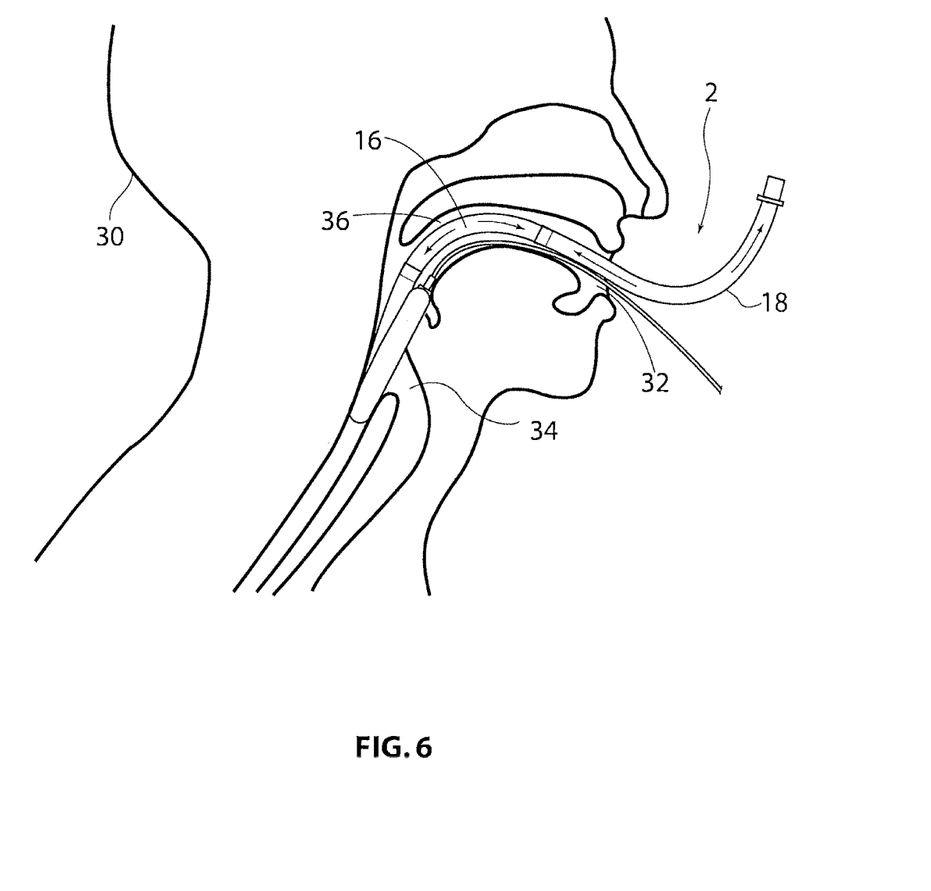
FIG. 6 schematically shows the artificial airway of the invention inserted in a patient.

Also the angle A is typically about 100°. FIG. 6 shows the artificial airway 2 deployed in a patient 30. In use, the user of the airway 2 grasps the curved portion 16 and inserts it through the mouth 32 of the patient and locates the mask 4 so that it surrounds the laryngeal opening 34. The cuff 10 can then be inflated so as to form a seal against the laryngeal opening. It will be seen that the curve of the curved portion 16 generally follows the anatomy of the patient and the convex side of the curved portion 16 is seated against the posterior pharynx 36 thus tending to stabilise the position of the mask in the patient. The straight portion 18 however can be moved inside the mouth cavity to allow good access for surgical procedures.

Many modifications will be apparent to those skilled in the art without departing from the spirit and scope of the invention.

The invention claimed is:

1. A laryngeal mask artificial airway comprising:
an airway tube having proximal and distal ends; and
a mask mounted at the distal end of the airway tube,
wherein the airway tube includes a curved portion adjacent to its distal end and a straight portion extending from the curved portion to the proximal end of the airway tube, wherein the curved portion is more rigid than the straight portion and is molded from a first material which is less flexible than a second material from which the straight portion is molded, the curved rigid portion consisting solely of a molded airway tube of annular cross-section and the straight portion being of annular cross-section, the curved portion and straight portion having a circular inner and outer surface, wherein the curved portion and the straight portion are separately molded, and
wherein a proximal end of the curved portion and a distal end of the straight portion are joined together, wherein the proximal end of the curved portion is tapered to provide a smooth transition between the curved portion and the straight portion.

2. The artificial airway according to claim 1 wherein the Shore A hardness of the first material is 40 to 50 and the Shore A hardness of the second material is 30 to 40.

3. The artificial airway according to claim 2 wherein the outer diameter of the curved portion is in the range 15 to 17 mm.

4. The artificial airway according to claim 1 wherein an outer diameter of the curved portion is greater than an outer diameter of the straight portion.

5. The artificial airway according to claim 4 wherein the outer diameter of the curved portion is in the range 15 to 17 mm.

6. The artificial airway according to claim 5 wherein a wall thickness of the curved portion is in the range 3 to 3.2 mm.

7. The artificial airway according to claim 4 wherein the outer diameter of the straight portion is in the range 11 to 13 mm.

8. The artificial airway according to claim 7 wherein a wall thickness of the straight portion is in the range 1.4 to 1.5 mm.

9. The artificial airway according to claim 4 wherein the straight portion includes a supporting spring to help prevent occlusion thereof.

10. The artificial airway according to claim 1 wherein the modulus of elasticity of the curved portion is greater than the modulus of elasticity of the straight portion.

11. The artificial airway according to claim 10 wherein the modulus of elasticity of the sample of the curved portion is about 1.5 to 5 times greater than that of the straight portion.

12. The artificial airway according to claim 11 wherein the modulus of elasticity of the sample of the curved portion is about 2.5 times greater than that of the straight portion.

13. The artificial airway according to claim 1, wherein the mask is a laryngeal mask.

14. An airway tube for a laryngeal mask artificial airway, the airway tube comprising proximal and distal ends configured such that, in use, a mask is mounted at the distal end, wherein the airway tube includes a curved portion adjacent to its distal end and a straight portion extending from the curved portion to the proximal end of the airway tube, wherein the curved portion is more rigid than the straight portion and is molded from a first material which is less flexible than a second material from which the straight portion is molded, the curved rigid portion consisting solely of a molded airway tube of annular cross-section and the straight portion being of annular cross-section, the curved portion and straight portion having a circular inner and outer surface, wherein the curved portion and the straight portion are separately molded, and
wherein a proximal end of the curved portion and a distal end of the straight portion are joined together, and wherein the proximal end of the curved portion is tapered to provide a smooth transition between the curved portion and the straight portion.

15. The airway tube according to claim 14 wherein the Shore A hardness of the first material is 40 to 50 and the Shore A hardness of the second material is 30 to 40.

16. The airway tube according to claim 14, wherein the proximal end is configured for insertion into a laryngeal opening.

* * * * *